(12) United States Patent
Krespi et al.

(10) Patent No.: US 8,721,696 B2
(45) Date of Patent: May 13, 2014

(54) SELECTIVE TREATMENTS FOR CHRONIC RHINOSINUSITIS

(75) Inventors: Yosef Krespi, New York, NY (US); Victor Z. Kizhner, New York, NY (US)

(73) Assignee: Valam Corporation, New York, NY (US)

( * ) Notice: Subject to any disclaimer, the term of this patent is extended or adjusted under 35 U.S.C. 154(b) by 521 days.

(21) Appl. No.: 12/840,397

(22) Filed: Jul. 21, 2010

(65) Prior Publication Data
US 2011/0021971 A1    Jan. 27, 2011

Related U.S. Application Data

(60) Provisional application No. 61/227,121, filed on Jul. 21, 2009.

(51) Int. Cl.
*A61N 5/06*    (2006.01)
*A61F 2/00*    (2006.01)

(52) U.S. Cl.
USPC ............................... 607/89; 607/99; 607/100

(58) Field of Classification Search
USPC ............ 607/88–94, 99, 100; 604/20; 128/898
See application file for complete search history.

(56) References Cited

U.S. PATENT DOCUMENTS

| | | | |
|---|---|---|---|
| 6,223,426 B1 * | 5/2001 | Kimmelmann et al. | 29/771 |
| 6,238,426 B1 * | 5/2001 | Chen | 607/88 |
| 6,358,272 B1 * | 3/2002 | Wilden | 607/89 |
| 2005/0107853 A1 | 5/2005 | Krespi et al. | |
| 2009/0093865 A1 | 4/2009 | Krespi et al. | |

FOREIGN PATENT DOCUMENTS

| WO | WO 96/36396 | 11/1996 |
|---|---|---|
| WO | WO 02/087698 | 11/2002 |
| WO | WO 03/013653 | 2/2003 |
| WO | WO 2004/096074 | 11/2004 |
| WO | WO 2005/018475 | 3/2005 |
| WO | WO 2006/081312 | 8/2006 |
| WO | WO 2007/109496 | 9/2007 |
| WO | WO 2007/127894 | 11/2007 |

OTHER PUBLICATIONS

Huckleby et al, Chromophore Enhanced Bacterial Photothermolysis, 1999, SPIE Conference on Lasers and Biophotonics in Veterinary, SPIE vol. 3590, pp. 375-385.*
Nussbaum, et al., "Effects of Low-Level laser Therapy (LLLT) of 810 nm upon in Vitro Growth of Bacteria: Relevance of Irradiance and Radiant Exposure", Journal of Clinical Laser Medicine & Surgery, vol. 21, No. 5, 2003, pp. 283-290.
Neuman, et al., "Characterization of Photodamage to *Escherichia coli* in Optical Traps", Biophysical Journal, vol. 77, Nov. 1999, pp. 2856-2863.
Jori, et al., "Photodynamic Therapy in the Treatment of MIcrobial Infections: Basic Principles and Perspective Applications", Lasers in Surgery and Medicine, 38, 2006, pp. 468-481.
Magnusson, et al., "The in-vitro effect of temperature on MICs, bactericidal rates and postantibiotic effects in *Staphylococcus aureus*, *Klebsiella pneumoniae* and *Pseudomonas aeruginosa*", Journal of Antimicrobial Chemotherapy, 35, 1995, pp. 339-343.
Bornstein, et al., "Near-infrared Photoinactivation of Bacteria and Fungi at Physiologic Temperatures", Photochemistry and Photobiology, 85, 2009, pp. 1364-1374.
Morgan, et al., "The effect of phototherapy on neutrophils", International Immunopharmacology, 9, 2009, pp. 383-388.
Brook, "Acute and Chronic Bacterial Sinusitis", Infectious Disease Clinics of North America, 21, 2007, pp. 427-448.
Jiang, et al., "Revision Functional Endoscopic Sinus Surgery", Annals of Otology, Rhinology & Laryngology, 111, 2002, pp. 155-159.
Palmer, et al., "Medical management in functional endoscopic sinus surgery failures", Current Opinion in Otolaryngology & Head and Neck Surgery, 11, 2003, pp. 6-12.
Engel, et al., "Light-Induced Decomposition of Indocyanine Green", Investigative Ophthalmology & Visual Science, vol. 49, No. 5, May 2008, pp. 1777-1783.
Tuchin, et al., "A Pilot Study of ICG Laser Therapy of Acne Vulgaris: Photodynamic and Photothermaolysis Treatment", Lasers in Surgery and Medicine, 33, 2003, pp. 296-310.
Omar, et al., "Lethal photosensitization of wound-associated microbes using indocyanine green and near infrared light", BMC Microbiology, 8, 111, Jul. 2008, pp. 1-10.
Krespi, et al., "Laser disruption and killing of methicillin-resistant *Staphylococcus aurreus* biofilms", American Journal of Otolaryngology, vol. 32, No. 3, 2011, pp. 198-202.
Krespi, et al., "Laser-induced microbial reduction in acute bacterial rhinosinusitis", American Journal of Rhinology & Allergy, 23, 2009, pp. e-29-e32.
Lund, et al., "Quntification for Staging Sinusitis", Annals of Otology, Rhinology & Layngology, 167, 1995, pp. 17-21.
Abels, et al., "Indocyanine green (ICG) and laser irradiation induce photooxidation", Archives of Dermatological Research, 292, 2000, pp. 4040-4411.
Sobanko, et al., "Efficacy of Low-Level Laser Therapy for Chronic Cutaneous Ulceration in Humand: A Review and Discussion", Dermatologic Surgery, 34, 2008, pp. 991-1000.
Guffey et al., "Effects of Combined 405-nm and 880-nm Light on *Staphylococcus aureus* and *Pseudomonas aeruginosa* in Vitro", Photomedicine and Laser Surgery, vol. 24, No. 6, 2006, pp. 680-683.
Fickweiler, et al., "Indocyanine green: Intacellular uptake and phototherpeutic effects in vitro", Journal of Photochemistry, and Photobiology B: Biology, 38, 1997, pp, 178-183.

(Continued)

*Primary Examiner* — Armando Rodriguez
(74) *Attorney, Agent, or Firm* — K&L Gates LLP

(57) ABSTRACT

Method for treating chronic rhinosinusitis in a human patient. In the method a photosensitizing agent such as indocyanine green can be applied to color a nasal or sinal treatment site harboring infectious microorganisms. The photosensitizing agent can have an energy absorption peak in a near infrared wavelength region of the electromagnetic spectrum. The method can also include applying light energy from a laser source at a near infrared wavelength or wavelengths to the colored treatment site, for a duration sufficient to control the microorganisms. Apparatus for performing the method is also disclosed.

17 Claims, No Drawings

(56) References Cited

OTHER PUBLICATIONS

Saikia, et al., "Safety Testing of Indocyanine Green in an Ex Vivo Porcine Retina Model", Investigative Ophthalmology & Visual Science, Vo. 47, No. 11, Nov. 2006, pp. 4998-5003.

Mukerji, et al., "Probiotics as adjunctive treatment for chronic rhinosinusitis: A randomized controlled trial", Otolaryngology—Head and Neck Surgery, 140, 2009, pp. 202-208.

Meltzer et al., "Rhinosinusitis: Developing guidance for cinical trials", J Allergy Clin Immunol, vol. 118, No. 5, Nov. 2006, pp. S17-S61.

Meltzer, et al., "Rhinosinusitis: Developing guidance for clinical trials", Supplement, Otolaryngology—Head and Neck Surgery, 135, 2006, pp. S31-S80.

International Search Report and the Written Opinion dated Jun. 18, 2008 for International Application No. PCT/US2007/085731.

Mupirocin Ointment, 2%, FDA 2002, NDA 50-788, pp. 3-7.

"Asymptomatic nasal carriage of mupirocin-resistant, . . . ", Clin Infect Dis. Jan. 15, 2003:36(2):e26-8. Epub Jan. 6, 2003. PubMed, A service of the National Library of Medicine.

Perl, et al., "Intranasal Mupirocin to Prevent Postoperative . . . ", The New England Journal of Medicine, vol. 346:1871-1877, Jun. 13, 2002, No. 24, downloaded Nov. 15, 2006.

Harbarth et al. "Randomized, placebo-controlled, double-blind trial to evaluate the efficacy of mupirocin for eradicating carriage of methicillin-resistant *Staphylococcus aureus*", Antimicrob Agents Chemother Jun. 1999; 43(6), pp. 1412-1416.

Loeb, et al. "Antimicrobial drugs for treating methicillin-resistant *Staphylococcus aureus* colonization." Cochrane Database Syst Rev 2003, 4, pp. 1-33.

Miller, et al. "Development of mupirocin resistance among methicillin-resistant *Staphylococcus aureus* after widespread use of nasal mupirocin ointment." Infect Control Hosp Epidemiol, Dec. 1996, 17(12), pp. 811-813.

Embleton, et al. "Selective lethal photosensitization of methicillin-resistant *Staphylococcus aureus* using an IgG-tin (IV) chlorin e6 conjugate." J Antimicrob Chemother, Dec. 2002, 50(6), pp. 857-864.

Embleton, et al. "Development of a novel targeting system for lethal photosensitization of antibiotic-resistant strains of *Staphylococcus aureus*." Antimicrob Agents Chemother Sep. 2005:49(9), pp. 3690-3696.

Johnston "Technology insight: ablative techniques for Barrett's esophagus—current and emerging trends." Nat Clin Pract Gastroenterol Hepatol Jul. 2005, 2(7), pp. 323-330.

\* cited by examiner

SELECTIVE TREATMENTS FOR CHRONIC RHINOSINUSITIS

CROSS-REFERENCE TO A RELATED APPLICATION

This application claims the benefit of provisional patent application No. 61/227,121, filed on 21 Jul. 2009, the entire disclosure of which is incorporated by reference herein.

STATEMENT REGARDING FEDERALLY SPONSORED RESEARCH OR DEVELOPMENT (Not applicable.)

The present invention relates, inter alia, to selective methods for the treatment of chronic rhinosinusitis and to treatment systems therefor.

BACKGROUND OF THE INVENTION

Chronic rhinosinusitis is a common disorder which may affect up to 13% of the US population. Chronic rhinosinusitis affects numerous quality-of-life factors including sense of smell, ability to sleep and ability to communicate. One common treatment for medical refractory chronic rhinosinusitis is functional endoscopic sinus surgery. As the disease course is indolent, yet prolonged, some medical treatment guidelines suggest use of an antibiotic treatment, prescribed following appropriately obtained nasal cultures, which treatment can last weeks with or without an adjunctive topical or oral steroid treatment. While effective in many cases, there are failures with functional endoscopic sinus surgery which, as described in the art, can be as high as 2-24 percent. It has been suggested that functional endoscopic sinus surgery may offer little, if any, greater benefit than medical management.

Furthermore, ineffective functional endoscopic sinus surgery may lead to the emergence of a new flora of pathogens. In one case, the bacterial flora in chronic rhinosinusitis comprises coagulase-negative *Staphylococci* as the most common of the organisms identifiable isolates, followed by *Staphylococcus aureus, Streptococcus viridans, Corynebacterium*, and anaerobes. Patients not relieved by primary functional endoscopic sinus surgery can demonstrate a significant rise in *Pseudomonas* and methicillin-resistant *Staphylococcus aureus* positive cultures. Moreover patients with *Staphylococcus aureus* and *Pseudomonas aeruginosa* positive cultures may be associated with an unfavorable evolution after surgery for chronic rhinosinusitis.

United States Patent Application No. 2005/0107853 to Krespi et al. describes various methods and apparatus for broad-spectrum treatments of chronic rhinosinusitis with various electromagnetic radiative energy including visible, and optionally, thermal RF, microwave or other longer energy wavelengths.

The foregoing description of background art may include insights, discoveries, understandings or disclosures, or associations together of disclosures, that were not known to the relevant art prior to the present invention but which were provided by the invention. Some such contributions of the invention may have been specifically pointed out herein, whereas other such contributions of the invention will be apparent from their context. Merely because a document may have been cited here, no admission is made that the field of the document, which may be quite different from that of the invention, is analogous to the field or fields of the present invention.

BRIEF SUMMARY OF THE INVENTION

The present invention provides, inter alia, an efficacious method for treating or controlling chronic rhinosinusitis which applies a photosensitizing agent and light energy to a nasal or sinal treatment site which is selective with regard to the characteristics of the photosensitizing agent and light energy employed and with regard to the duration and intensity of the treatment.

Useful embodiments of the invention can yield effective control of infectious microorganisms at the target site, with little or no pain or impairment of the sensitive functional tissues in nasal or sinus treatment regions.

In one aspect, the invention provides, a method of treating chronic rhinosinusitis in a human patient which comprises:
  applying a photosensitizing agent comprising indocyanine green to color a nasal or sinal treatment site harboring infectious microorganisms, the photosensitizing agent having an energy absorption peak in a near infrared wavelength region of the electromagnetic spectrum; and
  applying light energy from a laser source at a near infrared wavelength or wavelengths to the colored treatment site, for a duration sufficient to control the microorganisms.

DETAILED DESCRIPTION OF THE INVENTION

Bacterial killing can be effected by use of light-activated agents with exposure to appropriate light wavelengths, resulting in cytotoxicity by various mechanisms which may not yet be fully understood. Some mechanisms involved include the production of reactive oxygen species, for example singlet oxygen, and free radicals which can then exert a microbicidal effect. Such photo-activated disinfection is generally not expected to induce bacterial resistance as the method potentially provides a non-specific mechanism of cytotoxic action.

Accordingly, the invention also provides, a method of treating chronic rhinosinusitis in a human patient which comprises employing one or more or all of the following conditions:
  a dosage of indocyanine green sufficient to color tissue at the treatment site to be visibly green when viewed endoscopically, optionally a dosage of indocyanine green in the range of from about 10 µg to about 500 µg;
  light energy in a near infrared wavelength region of from about 780 nm to about 850 nm optionally from about 800 nm to about 820 nm or from about 800 nm to about 840 nm;
  light energy applied from a source outputting at a power of from about 2 W to about 15 W, optionally about 4 W to about 8 W;
  light energy applied for a duration of from about 30 seconds to about 480 seconds, optionally about from about 120 seconds to about 300 seconds;
  a light energy dosage of from about applied for a duration of from about 30 seconds to about 480 seconds, optionally about from about 120 seconds to about 300 seconds;
  an energy density at the treatment site, optionally within the nasal cavity, of from about 50 $J/cm^2$ to about 500 $J/cm^2$, optionally from about 100 $J/cm^2$ to about 300 $J/cm^2$; and
  repeating the application of photosensitizing agent and of the light energy from one to five additional times, optionally with a time interval between repeated photosensitizing agent and light energy applications of from about 3 days to about 14 days.

A suitable dosage of indocyanine green can be applied in any desired manner, for example, topically as a solution embedded into a sinomucosal applicator fabricated of cotton or the like. A suitable sinomucosal applicator can be soaked or otherwise impregnated with a desired dosage of indocyanine green and located in contact with a patient's nasal mucosal tissue and/or sinus mucosal tissue for a suitable period of time, for example from about one minute to about ten minutes. Other time periods such as from about 10 seconds to about 1 hour or more can be employed, if desired.

Methods according to the invention can comprise diffusing the applied light from an elongated source extending into the nasal cavity, for example, by diffusing the light laterally from an approximately cylindrical source in all or most radial directions. If desired the elongated source can be a diffusing optical fiber having a light emitting tip of suitable length, for example from about 10 mm to about 50 mm which can output light in radial directions, optionally all around the fiber, along the length of the tip. If desired, the elongated light source can be adapted with a suitable length, and/or curvature or shape, to reach through a patient's nostril into a sinus cavity to emit light into the sinus cavity after application of a suitable photosensitizing agent to same.

One suitable light applicator with a diffusing tip that can be employed in the practice of a method according to the present invention is illustrated in FIGS. 5 and 6 of United States Patent Application No. 2009/0093865 to Krespi et, the entire disclosure of which application is incorporated by reference herein. Other suitable light applicators will be known or apparent to a person of ordinary skill in the art, from the disclosure of United States Patent Application No. 2009/0093865 or in light of the disclosure herein, or will become known or apparent in the future, as the art develops.

If desired methods according to the invention can comprise taking a diagnostic tissue culture from the treatment site prior to application of a photosensitizing agent to determine the presence of one or more infectious microorganisms at the treatment site.

A patient can be selected for treatment according to the infectious microorganisms identified in the patient's culture.

Methods according to the invention can comprise collecting a tissue culture from the treatment site after the treatment and evaluating the efficacy of the treatment from the collected tissue culture.

Also, if desired, methods according to the invention can comprise applying one or more other photosensitizing agents in addition to or in place of indocyanine green, for example another photosensitizing agent or agents having a peak absorbency in the near infrared region. Some examples include green porphyrin, green mercocyanines, verteporfin, and zinc phthalocyanine. Such other photosensitizing agent optionally can appear visibly green when coated on a white substrate. Other suitable photosensitizing agents having an absorbency peak in the near infrared region, for example from about 750 nm to about 1000 nm can be employed, if desired, optionally photosensitizing agents that have a reflectance peak in the green region of the visible spectrum.

In another aspect the invention provides a treatment system for performing a method according to the invention which treatment system comprises a photosensitizing agent, a laser instrument, optionally a laser diode, to provide the light energy and a light applicator to transmit the light energy from the laser instrument to the treatment site all of which system components can be as described herein or as will be known or apparent to a person of ordinary skill in the art, in light of this disclosure, or will become known or apparent in the future, as the art develops, as being suitable for practicing one or more steps of a method according to the invention.

As an alternative to a laser diode, or other suitable laser source, a light-emitting diode ("LED") with comparable or equivalent energy output characteristics, or another narrow-band light source with suitable characteristics to generate appropriate illumination to stimulate the photosensitive agent, can be employed.

The invention includes any treatment apparatus adapted to perform one of the novel treatment methods described herein.

Indocyanine green is known as a useful agent for medical diagnostic study of hepatic, cardiac blood flow and retinal angiography after an intravenous injection. Indocyanine green is also known to bind to plasma proteins, to have low toxicity, and to be rapidly excreted, which properties can be useful in practicing some embodiments of the present invention. Indocyanine green is believed to have a light energy absorption peak at a wavelength of about 808 nm.

Low level laser therapy can be employed in a bactericidal treatment regimen utilizing single or compound light wave exposures.

In one example, laser energy exposures can be as low as 0.03 W/cm$^2$ employing an 810 nm laser to treat infections comprising *Pseudomonas* and/or *Staphylococcus aureus* or other target microorganisms.

Another example comprises reduction or eradication of *Staphylococcus aureus, Streptococcus pyrogenes* and/or *Pseudomonas aureginosa* by photoactivated disinfection employing indocyanine green at dosages in the range of from about 20 μg to about 200 μg activated with an infrared light wavelength of about 810 nm and a laser power setting not exceeding about 1.4 W/cm$^2$.

Methods and apparatus according to the invention can be employed to reduce or eradicate any microorganism present in the treated nasal or sinus cavity which is susceptible to the treatment including any of the microorganisms specifically mentioned elsewhere herein, fungi such as *Aspergillus* or *Alternaria* fungi, or *Candida, Enterobacteria*, anaerobic bacteria, *Propionibacterium* acnes, and other microorganisms as will be known or apparent to a person of ordinary skill in the art, in light of this disclosure, or will become known or apparent in the future, as the art develops. In many cases, or generally, a mixed population of microflora can be treated.

Usefully, low-level laser therapy, in some cases, can enhance wound healing, burns and healing of chronic wounds.

If desired, a method according to the invention can include taking one or more cultures from the patient, prior to treatment, to identify the microorganisms present at a treatment site. Also, if desired, the treatment parameters can be adjusted according to the species of microorganisms that are identified.

Cultures can be obtained in any suitable manner, for example, from nasal swabs taken under direct endoscopic visualization.

Any suitable laser light source can be employed, for example, a near infrared laser operable to output light in the range of 810-980 nm. Indocyanine green can be obtained from any suitable supplier, for example, Akorn, Buffalo Grove, Ill. Indocyanine green can be applied locally with any suitable total application, for example, not exceeding 2.5 mg per patient per treatment.

One example of a patient population suitable for treatment by a method according to the invention comprises patients with chronic rhinosinusitis who are failing medical management after endoscopic sinus surgery or before planned endoscopic sinus surgery.

Another example of a patient population suitable for treatment by a method according to the invention comprises patients with an established nasal culture of either *Staphylococcus aureus*, a *Streptococcus* species, *Pseudomonas aureginosa*, *Proteus mirabilis*, *H. influenza* or another intranasal pathogens. Such patients may also be exhibiting chronic rhinosinusitis and failing medical management after endoscopic sinus surgery or before planned endoscopic sinus surgery The following example is illustrative of the practice of a treatment method according to the invention.

EXAMPLE

A pledget soaked with an aqueous solution containing approximately 200 µg of indocyanine green is applied to each of a patient's nostrils. Promptly following removal of the pledget, a 30 mm optical diffuser fiber coupled to a near infrared diode laser set at 6 W is introduced intranasally radiating light circumferentially from the diffuser fiber allowing the light energy to reach all treatable areas. The laser is activated for 180 seconds. Assuming an average effective radius of the nasal cavity to be about 3 mm, the energy density within the nasal cavity is around 200 $J/cm^2$. Treatment can be repeated twice, 5-7 days apart. Cultures are collected at the end of each treatment.

One suitable form of pledget is a small, compress or wad of lint, cotton wool, or other soft absorbent material.

Other suitable applicators than a moistened pledget can be employed to apply the photosensitive agent, as will be known or apparent to a person of ordinary skill in the art, in light of this disclosure, or will become known or apparent in the future, as the art develops, for example a cotton swab or swabs, a spray device, a nasal spray, or an aerosol delivery device.

Other suitable diffusers can be employed in conjunction with an optical fiber or other light output device to generate a diffused light output in a desired nasal or sinus cavity, including other diffusers or diffuse light systems described in United States Patent Application No. 2009/0093865. For example a spherical, conical or other cylindrical diffuser can be employed. the diffuser can be formed of relatively rigid material or of flexible material, for example a balloon-like diffuser can be employed.

The above example is also illustrative of components employable in a system useful for practicing the illustrated method.

Embodiments of treatment methods according to the invention can help treat chronic rhinosinusitis through treating and controlling or reducing infection and promotion of mucosal healing.

Disclosures Incorporated. The entire disclosure of each and every United States patent and patent application, each foreign and international patent publication, of each other publication and of each unpublished patent application that is specifically referenced in this specification is hereby incorporated by reference herein, in its entirety. Should there appear to be conflict between the meaning of a term employed in the description of the invention in this specification and with the usage in material incorporated by reference from another document, the meaning as used herein is intended to prevail.

The foregoing detailed description is to be read in light of and in combination with the preceding background and invention summary descriptions wherein partial or complete information regarding the best mode of practicing the invention, or regarding modifications, alternatives or useful embodiments of the invention may also be set forth or suggested, as will be apparent to one skilled in the art.

The terms "include," "have," "has," and "contain," and their various grammatical forms, are to be understood as being open-ended and not to exclude additional, unrecited elements or method steps.

Throughout the description, where compositions instruments, devices apparatus, systems, or processes are described as having, including, or comprising specific components or elements, or in the case of processes, specific steps, it is contemplated that compositions instruments, devices apparatus, systems, or processes according to the present invention can also consist essentially of, or consist only of, the recited components, elements or steps.

In the application, where an element or component is said to be included in and/or selected from a list or group of recited elements or components, it should be understood that the element or component can be any one of the recited elements or components or can be selected from a group consisting of two or more of the recited elements or components.

The use of the singular herein is intended to include the plural (and vice versa) unless the context indicates otherwise. In addition, where the term "about" is used before a quantitative value, the specific quantitative value itself is intended to be included, unless specifically stated otherwise.

With regard to processes, it is to be understood that the order of steps or order for performing certain actions is immaterial so long as the described process remains operable. Moreover, two or more steps or actions may be conducted simultaneously, unless the context indicates otherwise. In addition, any proportions recited herein are to be understood to be proportions by weight, based upon the weight of the relevant composition, unless the context indicates otherwise.

The description of the invention is to be understood as including combinations of the various elements of the invention, and of their disclosed or suggested alternatives, including alternatives disclosed, implied or suggested in any one or more of the various methods, products, compositions, systems, apparatus, instruments, aspects, embodiments, examples described in the specification or drawings, if any, and to include any other written or illustrated combination or grouping of elements of the invention or of the possible practice of the invention, except for groups or combinations of elements that are incompatible with, or contrary to the purposes of the invention, as will be or become apparent to a person of ordinary skill.

The present invention includes the examples and embodiments described herein and other specific forms that embody the spirit or essential characteristics of the invention or of the respective described example or embodiment. The foregoing examples and embodiments are in all respects intended to be illustrative of the invention described herein. It is to be understood that many and various modifications of the invention, or of an example or embodiment of the invention described herein will be apparent to those of ordinary skill in the relevant art, or may become apparent as the art develops, in the light of the foregoing description. Such modifications are contemplated as being within the spirit and scope of the invention or inventions disclosed herein.

The invention claimed is:

1. A method of treating chronic rhinosinusitis in a human patient, the method comprising:
    applying a photosensitizing agent comprising indocyanine green to color a nasal or sinal treatment site harboring infectious microorganisms, the photosensitizing agent having an energy absorption peak in a near infrared wavelength region of the electromagnetic spectrum; and
    applying light energy having an energy density from about 50 $J/cm^2$ to about 500 $J/cm^2$ from a laser source at a near infrared wavelength or wavelengths to the colored treatment site, for a duration sufficient to control the microorganisms.

2. A method according to claim 1 comprising employing one or more or all of the following conditions:
- a dosage of indocyanine green sufficient to color tissue at the treatment site to be visibly green when viewed endoscopically;
- light energy in a near infrared wavelength region of from about 780 nm to about 850 nm;
- light energy applied from a source outputting at a power of from about 2 W to about 15 W;
- light energy applied for a duration of from about 30 seconds to about 480 seconds;
- a light energy dosage applied for a duration of from about 30 seconds to about 480 seconds; and
- repeating the application of photosensitizing agent and of the light energy from one to five additional times.

3. A method according to claim 1 comprising diffusing the applied light from a source extending into the nasal cavity.

4. A method according to claim 1 comprising taking a diagnostic tissue culture from the treatment site prior to application of a photosensitizing agent to determine the presence of one or more infectious microorganisms at the treatment site.

5. A method according to claim 4 comprising selecting a patient for treatment according to the infectious microorganisms identified in the culture.

6. A method according to claim 1 comprising collecting a tissue culture from the treatment site after the treatment and evaluating the efficacy of the treatment from the collected tissue culture.

7. A method of treating chronic rhinosinusitis in a human patient, the method comprising:
- applying a photosensitizing agent having a peak absorbency in the near infrared region to color a nasal or sinal treatment site harboring infectious microorganisms, the photosensitizing agent optionally appearing visibly green when coated on a white substrate and having an energy absorption peak in a near infrared wavelength region of the electromagnetic spectrum; and
- applying light energy having an energy density from about 50 J/cm$^2$ to about 500 J/cm$^2$ from a laser source at a near infrared wavelength or wavelengths to the colored treatment site, for a duration sufficient to control the microorganisms.

8. A method according to claim 1 wherein a laser diode or a light-emitting diode provides the light energy and a light applicator transmits the light energy to the treatment site.

9. A method according to claim 1 wherein the applied indocyanine green is in the range of from about 10 μg to about 500 μg.

10. A method according to claim 1 wherein the light energy is applied from a source outputting at a power of from about 2 W to about 15 W.

11. A method according to claim 1 wherein an energy density at the treatment site is from about 100 J/cm$^2$ to about 300 J/cm$^2$.

12. A method according to claim 2 wherein the dosage of indocyanine green is in the range of from about 10 μg to about 500 μg.

13. A method according to claim 2 wherein the light energy is in a near infrared wavelength region of from about 800 nm to about 820 nm.

14. A method according to claim 2 wherein the light energy is applied from a source outputting at a power of from about 4 W to about 8 W.

15. A method according to claim 2 wherein the light energy is applied for a duration of from about 120 seconds to about 300 seconds.

16. A method according to claim 2 including a time interval between repeated photosensitizing agent and light energy applications of from about 3 days to about 14 days.

17. A method according to claim 3 comprising diffusing the light laterally in all or most radial directions from a source having an approximately cylindrical, conical, spherical, part-spherical or other suitable configuration.

\* \* \* \* \*